United States Patent [19]

Rasmussen

[11] 4,358,470
[45] Nov. 9, 1982

[54] PROCESS AND APPARATUS FOR THE TREATMENT OF SAMPLES WITH A SUCCESSION OF LIQUIDS

[75] Inventor: Soren W. Rasmussen, Copenhagen, Denmark

[73] Assignee: LKB-Produkter AB, Bromma, Sweden

[21] Appl. No.: 221,391

[22] Filed: Dec. 30, 1980

Related U.S. Application Data

[63] Continuation of Ser. No. 10,846, Feb. 8, 1979, abandoned.

[30] Foreign Application Priority Data

Feb. 10, 1978 [SE] Sweden ............................. 7801564

[51] Int. Cl.³ .................... A01G 5/06; A01M 1/00; A01M 3/00; C13C 13/08
[52] U.S. Cl. ............................... 427/4; 8/94.11; 118/50; 118/50.1; 118/421; 118/429; 118/688; 118/689; 118/690; 134/95; 134/98; 427/296
[58] Field of Search ................. 8/94.11; 118/50, 50.1, 118/421, 429, 688, 689, 690; 134/95, 98; 427/4, 296

[56] References Cited

U.S. PATENT DOCUMENTS

| | | | |
|---|---|---|---|
| 3,025,188 | 3/1962 | Larsh et al. | 427/104 |
| 3,227,130 | 1/1966 | Weiskopf | 118/697 |
| 3,446,423 | 5/1969 | Carroll | 137/565 |
| 3,557,077 | 1/1971 | Branfeldt et al. | 422/108 X |
| 3,604,436 | 9/1971 | Lipshaw | 134/76 |
| 3,725,010 | 4/1973 | Penhast | 422/64 |
| 3,859,046 | 1/1975 | Hurst et al. | 118/50 X |
| 3,895,138 | 7/1975 | Sewell et al. | 427/298 |
| 4,141,312 | 2/1979 | Louder et al. | 118/50 X |

Primary Examiner—Michael R. Lusignan
Attorney, Agent, or Firm—Fisher, Christen & Sabol

[57] ABSTRACT

Process and apparatus for the staining of biological samples in which fluids of differing specific densities are successively introduced to the samples comprises a closed chamber to receive the samples for treatment, the chamber being provided with flow passages at the top and bottom and is in communication with an under pressure generating device so that fluids may be introduced into the chamber either from the top or the bottom depending upon whether a succeeding fluid is of lesser, or greater, specific density than the preceding fluid.

8 Claims, 1 Drawing Figure

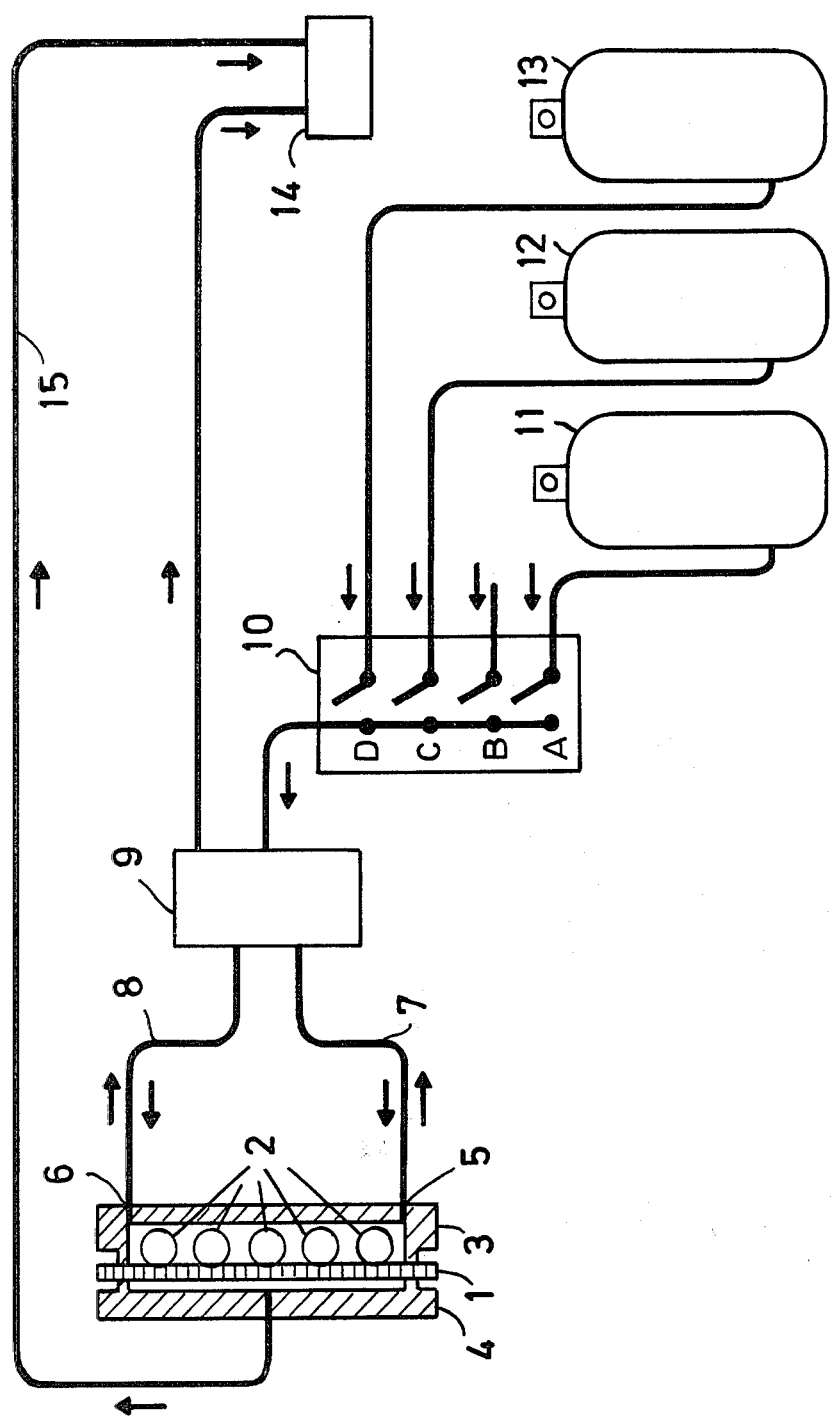

PROCESS AND APPARATUS FOR THE TREATMENT OF SAMPLES WITH A SUCCESSION OF LIQUIDS

This is a continuation of application Ser. No. 10,846, filed Feb. 8, 1979, now abandoned.

BACKGROUND OF THE INVENTION

The present invention refers to a device for preparation such as staining of biological samples.

The method which is commonly used for introducing contrasting material in sections of a biological specimen in electromicroscopy is a so-called double-staining in uranyl acetate and lead citrate. This staining is usually performed on drops of the staining solution in petri dishes, each section carrying grid being stained separately. In addition to the considerable amount of manual work involved when big series of sections are to be stained, the method is very sensitive to contaminations, deriving either from air born dirt particles or from different precipitates in the staining solutions or on the surface of the drop (for example lead carbonate from the reaction between lead citrate and carbon dioxide). Presumably most of the contaminations on the sections are obtained when the sections are applied on the top of the drop or when the sections are brought through the surface of the staining solution (when the grids are brought through the staining solutions). A further source of contamination is the transfer of the grids from the drop to a cleaning water bath. During this transfer, staining solution attached to the sections will be brought in contact with air. If the transfer is too slow and evaporation may occur on the surface layer, whereby precipitates of the staining solution, and/or reactions between carbon dioxide and lead citrate might give rise to contaminations on the sections. A description of these staining procedures known per se is given in the following publications:

Hayat, M. A.: Principles and techniques of electron microscopy. Biological applications, Vol. 1. Van Nostrand Reinhold comp., New York 1970, or Lewis, P. R., Knight, D. P.: Staining methods for sectioned material. Practical methods in electron microscopy Eds. A M. Glaubert, North-Holland Publishing Comp. 1977.

BRIEF SUMMARY OF THE INVENTION

It is an object of the present invention to provide a device which enables staining of as much as forty sections simultaneously under completely determined conditions. In addition to the time saving aspect the use of the device according to the invention eliminates the contaminations due to the contact between the surface of the staining liquid and the sections and furthermore, the contamination deriving from precipitates in the staining solution is considerably reduced. The characteristics of the invention will appear from the claims attached to the specification.

BRIEF DESCRIPTION OF THE FIGURE

The single FIGURE is a schematic diagram of a preferred embodiment of the invention.

The invention will now be described in detail, reference being made to the enclosed FIGURE which schematically shows a staining device according to the invention.

DETAILED DESCRIPTION OF THE INVENTION

In the device of the FIGURE, reference 2 denotes grids on which the sections to be stained are applied in a flexible plastic plate with 40 different slots in which the grids are fixed (Hiraoka staining kit, Polyscience Inc., Cat. No. 4635 B). When the grids are to be applied the plate is bent so as to open the slots whereafter the grids are inserted in the slots and the plate is brought back to its original shape whereby the grids are fixed. The plate 1 is thereafter mounted in a staining chamber consisting of two parts 3 and 4. The first part 3 is provided with a circular, 3.5 mm deep cavity which has a volume of approximately 3 ml and is provided with two bores, 5, 6 which are arranged at the bottom and the top of the chamber. The chamber is furthermore provided with a heating device not shown in the FIGURE in order to maintain a suitable temperature during the staining. The other part 4 of the chamber consists of a lid which attaches the plate 1 to the edge of the staining chamber, or removable closure means 3, whereby the plate also has a sealing function in the chamber. The two parts of the chamber are kept together by a locking device not shown in the drawing. The inputs and outputs 5 and 6, respectively, of the chamber are via two flexible tubes 7 and 8, respectively, connected to a valve 9 so that the upper and lower part, respectively, of the chamber are alternatively connectable to a pump 14 and a multipath valve 10. The multipath valve 10 is in the device shown in the FIGURE provided with four inputs, A B C D of which A is connected to a water container 11, the input B is connected to atmosphere, the input C is connected to a container 12 with one of the staining solutions such as uranyl acetate and the input B is connected to a container 13 containing the other staining liquid for instance lead citrate. The valve 9 is thereby designed so as to permit the flow from the valve 10 to pass via the bore 6 and out via the bore 5 and from there on to the pump 14 or to pass via the bore 5 and out via the bore 6 to the pump. This will thus mean that the chamber 3, 4 can be filled either from the top or from the bottom in dependance of the setting of the valve 9.

The difference of specific weight of the different staining liquids and the water to be used for cleaning will thereby determine the direction of flow through the chamber, i.e. the setting of valve 9. Thus, a solution having a higher density than the solution already in the chamber will always be supplied from the bottom whereas a solution with a lower density than the one already present in the chamber will be supplied from the top in order to obtain a fast and uniform change of solution.

The chamber 3, 4 is furthermore provided with another connection 15 to the pump 14 whereby an under pressure is obtained behind the plate 1 which prevents the plate from bending into the cavity 3.

The containers containing the staining solutions may consist of closed plastic bags which are protected from light and air by a thin aluminum layer. Before the solution is introduced into the plastic bags the solutions are degassed by means of heating. The containers are thereafter pressed together in order to eliminate residual gases and are thereafter sealed. The sealed plastic containers are connected to the valve via capillary tubings which are mounted into the containers after sealing. The use of sealed containers for the staining solutions offers two advantages as compared to the use of standard bottles. These containers prevent carbon dioxide to be in contact with the lead citrate solutions whereby the risk for precipitation of lead carbonate is eliminated. Furthermore, the bags are pressed together whereafter the solutions are used which prevents gases from being dissolved in the solutions. Gases will thus not be set free from the solutions during the staining procedure. If precautions are carried out to prevent adding of carbon dioxide during the preparation of the lead citrate solution, this solution could be left at room temperature connected to the device for several months without forming of precipitates and without any substantial decrease of the staining capacity. Furthermore, the uranyl acetate solution can be connected to the device during longer periods of time.

Concerning the valve 10, this valve should suitably be designed as indicated in the figure, i.e. with the water container connected to the valve in such a way that the water when connected flows through the complete valve.

The device hitherto described operates in the following manner. When the grids have been located in the staining chamber the first step of the staining procedure consists of a wetting of the sections in distilled water. It is thereby essential to avoid contaminations in the water used for this wetting and it is also essential that the staining chamber itself is as clean as possible, since particles from the water surface or on the walls of the chamber could be attached to the sections and be difficult to remove. The water is thereafter sucked out and replaced by air so that air bubbles on the chamber walls and the sections are removed. Thereafter the chamber is again filled with water. The water is sucked out and is simultaneously replaced by the uranyl acetate solution. The air/uranyl transfer which exists in the above described drop staining method is thus replaced by a water/uranyl acetate transfer whereby the risk for contamination from the surface of the staining solution is neglectable. The exchange of solutions is provided within about 30 seconds with the pump operating. During the staining the pump is stopped. If a staining with alcoholic uranyl acetate (more than 25 percent alcohol) is preferred, the direction of flow during filling and rinsing is changed, as an alcoholic 5 percent solution of uranyl acetate with more than 24 percent alcohol has a density less than 1. If heating is required during the uranyl acetate staining the desired temperature is set with a thermostate. The uranyl acetate staining is followed by a five minute cleaning in distilled water. The second staining is initiated by changing for a lead citrate solution. During the staining the pump is stopped. If desired a heating may take place during the lead citrate staining. Finally the chamber is emptied by replacing water by air. The net carrying grid is then removed from the chamber and the water remaining on the grid is removed by a piece of filter paper. It is of course possible to carry out the staining by using only one of the staining solutions by means of disconnecting the other solution. The chamber will then remain filled with water (with the pump stopped) during the filling and cleaning time.

The above described device eliminates most problems present when staining sections for electron microscopy. The contaminations usually appearing as different crystals, small granulates, amorphous precipitates etc., will not appear when the sections are stained in the device. Furthermore, it is possible in the device to supply heat during the lead citrate staining without having precipitates.

We claim:

1. Apparatus providing a closed system for the treatment of samples with a succession of liquids, such as the staining of biological samples, comprising:
    a closed chamber within which said samples are to be successively treated by said succession of liquids;
    said chamber including removable closure means for the insertion and removal of said samples;
    said chamber being provided with respective bores at the top and bottom thereof for the selective flow of fluid into the closed chamber through a respective one of said bores and the simultaneously outflow of fluid from the closed chamber through the respective other of said bores;
    a plurality of flexible-walled closed containers for supplying the respective liquids for treatment of said samples, each of said containers having an outlet for the discharge of contained liquid;
    flow controlling means including reversing valve means for selective connection with a respective one of the outlets of said flexible-walled containers and for selectively connecting said one outlet with one of the bores of the closed chamber to conduct the contained liquid into the chamber selectively at the top or the bottom of the chamber depending upon whether the ratio between the specific density of the succeeding liquid is higher or lower than the specific density of the preceding liquid, and;
    a source of vacuum having a pump and an inlet;
    said flow controlling means also including means for selectively connecting the inlet of the source of vacuum to the other bore of the closed chamber to induce flow of liquid from one of said containers into said chamber through said one bore from top to bottom or from bottom to top depending upon the density ratio between the succeeding and preceding liquids to flow through the chamber.

2. Apparatus of claim 1, wherein said flow controlling means include multiple shutoff valve means having a plurality of inlets for the respective sources of liquids all connected to a common outlet means connected, in turn, to said reversing valve means.

3. Apparatus of claim 2, wherein said shutoff valve means are connected to said outlet means in series, one of said liquids comprises a cleaning agent, and the shutoff valve means for said one liquid is connected farthest from the outlet means, whereby said cleaning agent will flow through all of the valve means when connected.

4. Process for the treatment of samples with a succession of liquids, such as the staining of biological samples comprising the steps:
    placing a sample to be treated into a closed chamber;
    placing each of the liquids into a separate closed supply vessel having a variable volume;
    filling each vessel with the selected one of said liquids and expelling gases therefrom;
    introducing a first liquid into said chamber from a supply vessel and filling the chamber completely to exclude gases therefrom;
    introducing a second liquid into said chamber from another supply vessel without introducing gas from the atmosphere and without mixing the first and second liquids while simultaneously withdrawing the liquid previously introduced into the chamber.

5. Process of claim 4, wherein a third liquid is introduced into said chamber from a supply vessel without introducing gas from the atmosphere while simultaneously withdrawing the second liquid from the chamber.

6. Process of claim 4, wherein the first liquid is withdrawn by subjecting it to a source of vacuum and the second liquid is introduced as a result of atmospheric pressure acting on said variable volume vessel.

7. Process of claim 6, wherein said variable volume vessel is a closed container having a collapsible wall.

8. Process of any one of claims 4, 5, 6 or 7, wherein said closed chamber is provided with a first bore at the top and a second bore at the bottom, and a succeeding light is introduced through one of the bores while the preceding liquid is withdrawn through the other bore, the succeeding liquid being introduced through the first bore if its specific density is less than that of the preceding light and being introduced through the second bore if its specific density is greater than that of the preceding liquid.

* * * * *